(12) United States Patent
Masago et al.

(10) Patent No.: US 7,839,505 B2
(45) Date of Patent: Nov. 23, 2010

(54) OPTICAL ROTATING POWER MEASUREMENT METHOD AND OPTICAL ROTATING POWER MEASUREMENT APPARATUS

(75) Inventors: Hisashi Masago, Hachioji (JP); Tomoyuki Fukazawa, Hachioji (JP); Mutsumi Senuma, Hachioji (JP); Atsushi Yamada, Hachioji (JP); Yuji Fujisawa, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 374 days.

(21) Appl. No.: 12/034,032

(22) Filed: Feb. 20, 2008

(65) Prior Publication Data

US 2008/0204751 A1 Aug. 28, 2008

(30) Foreign Application Priority Data

Feb. 22, 2007 (JP) ............................. 2007-041804

(51) Int. Cl.
*G01J 4/00* (2006.01)
(52) U.S. Cl. ..................................................... 356/367
(58) Field of Classification Search .......... 356/367–370
See application file for complete search history.

(56) References Cited

FOREIGN PATENT DOCUMENTS

JP           6-3259         1/1994

OTHER PUBLICATIONS

Japanese Patent Abstract Publication No. 2000-046732 published Feb. 18, 2000, one page.
"Test methods for optical rotation of chemical products," Japanese Industrial Standard, K 0063-1992, pp. 1-10.
Japanese Patent Abstract Publication No. 06-003259 published Jan. 11, 1994, eight pages.
Hvidt et al., "Temperature-Dependent Optical Rotatory Dispersion Properties of Helical Muscle Proteins and Homopolymers,"Biopolymers, vol. 24, pp. 1647-1662, Sep. 1985.
Herreros-Cedres et al., "Temperature-dependent gyration tensor of LilO3 single crystal using the high-accuracy universal polarimeter," Journal of Applied Crystallography, vol. 35, Apr. 2002, pp. 228-232.
Japanese Patent Abstract; Publication No. 2000046732; Publication Date Feb. 18, 2000.
K. Wiberg et al.; "Temperature Dependence of Optical Rotation: α-Pinene, Pinane, Camphene, Camphor, and Fenchone"; J. Phys. Chem. A 2004; vol. 108; pp. 5559-5563.
Extended European Search Report for European Application No. 08151738.5; 6 pages; Dated Jul. 9, 2008.

*Primary Examiner*—F. L Evans
(74) *Attorney, Agent, or Firm*—Rankin, Hill & Clark LLP

(57) ABSTRACT

An optical rotating power measurement method comprising: an optical rotating power data acquisition step of starting measurement of the optical rotating power of the sample in a measurement apparatus during a temperature changing process where a controller controls the temperature of the sample such that the temperature reaches the predetermined temperature and of obtaining temperature data and optical rotating power data of the sample as time passes during the temperature changing process; and a data processing step of obtaining a straight line relationship data between the temperature data and the optical rotating power data, by using the fact that the optical rotating power of the sample is proportional to a measurement temperature; wherein the optical rotating power data of the sample at the predetermined temperature or the temperature dependence data of the optical rotating power of the sample is determined based on the straight line relationship data.

5 Claims, 6 Drawing Sheets

US 7,839,505 B2

OPTICAL ROTATING POWER MEASUREMENT METHOD AND OPTICAL ROTATING POWER MEASUREMENT APPARATUS

RELATED APPLICATIONS

This application claims the priority of Japanese Patent Application No. 2007-41804 filed on Feb. 22, 2007, which is incorporated herein by reference.

FIELD OF THE INVENTION

The present invention relates to optical rotating power measurement methods and optical rotating power measurement apparatuses, and more particularly, to speedup and S/N ratio improvement in optical rotating power measurements.

BACKGROUND OF THE INVENTION

Organic materials rotate the plane of polarization of incident linearly polarized light. Therefore, by measuring the optical rotating power thereof, the materials can be identified or optical isomers can be distinguished.

For these purposes, the optical rotating power of the materials has been measured, for example, according to Japanese Industrial Standard (JIS) K 0063 (pages 669 to 673).

In optical rotating power measurements, since a signal to be detected is very low, a S/N ratio that is higher than in general measurements has been demanded. To meet this demand, conventional optical rotating power measurements start after waiting for the sample to reach a predetermined temperature and stabilize at the predetermined temperature, as disclosed, for example, in Japanese Unexamined Patent Application Publication No. 2000-46732.

With this procedure, however, it takes much time until the sample reaches the predetermined temperature.

There has been a strong demand in the optical rotating power measurement field for a technique that realizes both speedup and S/N ratio improvement. Conventionally, such a technique was not found.

SUMMARY OF THE INVENTION

Accordingly, it is an object of the present invention to provide an optical rotating power measurement method and an optical rotating power measurement apparatus that realize both speedup and S/N ratio improvement in optical rotating power measurements.

The inventors of the present application have extensively studied measurement of the optical rotating power and found that both speedup and S/N ratio improvement in the measurement can be ensured by using optical rotating power data of the sample obtained during a temperature changing process during which the temperature of the sample changes to reach a predetermined temperature, based on the fact that the optical rotating power of the sample is proportional to the measurement temperature. The inventors thus made the present invention.

The foregoing object is achieved in one aspect of the present invention through the provision of an optical rotating power measurement method for obtaining optical rotating power data of a sample at a predetermined temperature by using an optical rotating power measurement apparatus provided with a sample temperature controller for controlling the temperature of the sample such that the temperature reaches the predetermined temperature.

The optical rotating power measurement method includes an optical rotating power data acquisition step and a data processing step.

In the optical rotating power data acquisition step, measurement of the optical rotating power of the sample is started in the optical rotating power measurement apparatus during a temperature changing process where the sample temperature controller controls the temperature of the sample such that the temperature reaches the predetermined temperature, and temperature data and optical rotating power data of the sample are obtained over time during the temperature changing process.

In the data processing step, a straight line relationship data between the temperature data and the optical rotating power data obtained in the optical rotating power data acquisition step is obtained by using the fact that the optical rotating power of the sample is proportional to a measurement temperature.

Then, the optical rotating power data of the sample at the predetermined temperature or the temperature dependence data of the optical rotating power of the sample is determined based on the straight line relationship data between the temperature data and the optical rotating power data of the sample during the temperature changing process.

It is preferred in the present invention that a regression straight line data between the temperature data and the optical rotating power data obtained in the optical rotating power data acquisition step be obtained as the straight line relationship data in the data processing step.

It is preferred in the present invention that the straight line relationship data be obtained by using temperature data and optical rotating power data of the sample, obtained in an allowable range of the predetermined temperature during the temperature changing process in the data processing step.

It is preferred in the present invention that the allowable range of the predetermined temperature be determined based on the temperature dependence data of the optical rotating power of the sample in the data processing step.

The foregoing object is achieved in another aspect of the present invention through the provision of an optical rotating power measurement apparatus for obtaining optical rotating power data of a sample at a predetermined temperature.

The optical rotating power measurement apparatus includes a sample temperature controller for controlling the temperature of the sample such that the temperature reaches the predetermined temperature, an optical rotating power data acquisition unit, and a data processing unit.

The sample temperature controller includes an adjustable temperature cell holder. The adjustable temperature cell holder holds a sample cell while controlling the temperature of the sample such that the temperature reaches the predetermined temperature.

The optical rotating power data acquisition unit starts measurement of the optical rotating power of the sample in the optical rotating power measurement apparatus during a temperature changing process where the sample temperature controller controls the temperature of the sample such that the temperature reaches the predetermined temperature and obtains temperature data and optical rotating power data of the sample over time during the temperature changing process.

The data processing unit obtains a straight line relationship data between the temperature data and the optical rotating power data obtained by the optical rotating power data acquisition unit, by using the fact that the optical rotating power of the sample is proportional to a measurement temperature.

Then, the optical rotating power data of the sample at the predetermined temperature or the temperature dependence data of the optical rotating power of the sample is determined based on the straight line relationship data between the temperature data and the optical rotating power data of the sample during the temperature changing process.

It is preferred in the present invention that the adjustable temperature cell holder include a Peltier device. The Peltier device adjusts the temperature of the sample disposed in the sample cell.

It is preferred in the present invention that the adjustable temperature cell holder include a positioning unit. The positioning unit positions the adjustable temperature cell holder such that a measurement axis located at the center of the sample cell is positioned on a predetermined optical path of the optical rotating power measurement apparatus.

According to an optical rotating power measurement method and an optical rotating power measurement apparatus of the present invention, the optical rotating power data of a sample at a predetermined temperature or the temperature dependence data of the optical rotating power of the sample is determined based on a straight line relationship data between temperature data and optical rotating power data of the sample during a temperature changing process during which the temperature of the sample reaches the predetermined temperature. As a result, the present invention reliably provides both speedup and S/N ratio improvement in optical rotating power measurements.

In the present invention, when a regression straight line data is obtained as the straight line relationship data, both speedup and S/N ratio improvement are achieved more reliably in optical rotating power measurements.

In the present invention, when the straight line relationship data is obtained by using temperature data and optical rotating power data in an allowable range of the predetermined temperature during the temperature changing process, both speedup and S/N ratio improvement are achieved more reliably in optical rotating power measurements.

In the present invention, when the allowable range of the predetermined temperature is determined based on the temperature dependence data of the optical rotating power of the sample, both speedup and S/N ratio improvement are achieved more reliably in optical rotating power measurements.

According to an optical rotating power measurement apparatus of the present invention, when the adjustable temperature cell holder includes the Peltier device or the positioning unit, both speedup and S/N ratio improvement are achieved more reliably in optical rotating power measurements.

DESCRIPTION OF THE PREFERRED EMBODIMENT

An embodiment of the present invention will be described below with reference to the drawings.

Figure 1:
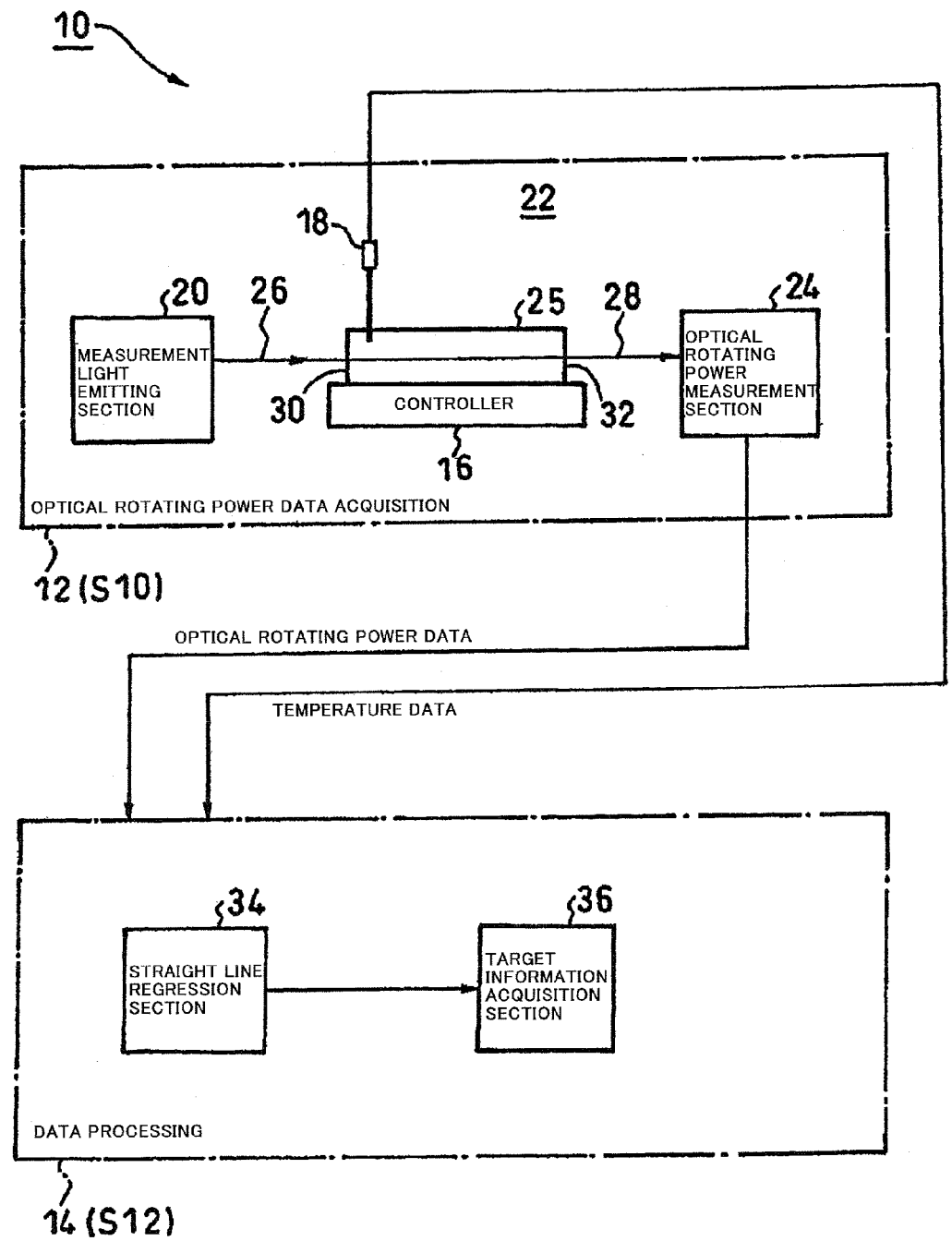
FIG. 1 is a view showing, in outline, the structure of an optical rotating power measurement apparatus which uses an optical rotating power measurement method according to an embodiment of the present invention.

FIG. 1 shows, in outline, the structure of an optical rotating power measurement apparatus 10 that uses an optical rotating power measurement method according to an embodiment of the present invention.

The optical rotating power measurement apparatus 10 includes an optical rotating power data acquisition unit 12 and a data processing unit 14.

The optical rotating power data acquisition unit 12 performs an optical rotating power data acquisition step (S10).

Specifically, the optical rotating power data acquisition unit 12 starts measuring the optical rotating power of a sample in the optical rotating power measurement apparatus 10 during a temperature changing process in which the temperature of the sample is changed to a predetermined temperature by a sample temperature controller 16, and obtains temperature data and optical rotating power data of the sample at predetermined time intervals in the temperature changing process.

The data processing unit 14 is formed, for example, of a computer and performs a data processing step (S12).

Specifically, the data processing unit 14 obtains a regression straight line data (straight line relationship data) between the temperature data and the optical rotating power data obtained by the optical rotating power data acquisition unit 12, by using the fact that the optical rotating power of the sample is proportional to the measurement temperature. Then, the data processing unit 14 determines the optical rotating power data of the sample at a predetermined temperature (for example, at 20° C.) by using the regression straight line data.

<Optical Rotating Power Data Acquisition Unit>

Next, the optical rotating power data acquisition unit 12 will be described in detail.

The optical rotating power data acquisition unit 12 includes a measurement light emitting section 20, a sample section 22, and an optical rotating power measurement section 24.

The measurement light emitting section 20 includes, for example, a light source, a polarizer, and a modulator, and emits measurement light 26 onto the sample placed in a sample cell 25.

The sample section 22 includes, for example, the sample cell 25. The sample is disposed in the sample section 22, and the sample section 22 is disposed such that the measurement light 26 coming from the measurement light emitting section 20 passes through the sample.

The optical rotating power measurement section 24 includes, for example, an analyzer and a detector, and obtains data about the optical rotating power of the sample from light 28 that has passed through the sample.

<Sample Section>

The sample section 22 will be described below in detail.

The sample section 22 includes the sample cell 25, a sample temperature sensor 18, and the sample temperature controller 16.

The sample cell 25 holds the sample whose optical rotating power is to be measured and has windows 30 and 32 through which the measurement light 26 and the light 28 pass.

The sample temperature sensor 18 detects the temperature of the sample placed in the sample cell 25.

The sample temperature controller 16 is formed, for example, of a thermoelectric-effect device or a thermostatic circulation chamber and controls the temperature of the sample disposed in the sample cell 25 so as to be equal to a measurement temperature data specified in advance.

<Data Processing Unit>

The data processing unit 14 will be described below in detail.

The data processing unit 14 includes a straight line regression section 34 and a target information acquisition section 36 and determines the optical rotating power data of the sample from the optical rotating power data obtained by the optical rotating power measurement section 24.

The straight line regression section 34 obtains a regression straight line data (gradient data and intercept data) between the temperature data and optical rotating power data obtained by the optical rotating power data acquisition unit 12.

The target information acquisition section 36 determines the optical rotating power data of the sample at the predetermined temperature (for example, at 20° C.) by using the regression straight line data (gradient data and intercept data) obtained by the straight line regression section 34.

The optical rotating power measurement apparatus 10, which uses an optical rotating power measurement method according to the present embodiment, is configured as described in outline above. The operation thereof will be described next.

<Optical Rotating Power Data Acquisition Step>

When the sample is placed in the sample cell 25 and the sample temperature controller 16 starts controlling the temperature of the sample so as to be equal to the predetermined temperature, the optical rotating power data acquisition unit 12 immediately starts measuring the optical rotating power of the sample placed in the sample cell 25.

Specifically, in the optical rotating power data acquisition step (S10), the optical rotating power data acquisition unit 12 starts measuring the optical rotating power of the sample in the temperature changing process, during which the sample temperature controller 16 changes the temperature of the sample to the predetermined temperature, and obtains optical rotating power data at predetermined time intervals while the sample temperature sensor 18 monitors the temperature data of the sample in the temperature changing process.

<Data Processing Step>

The data processing step (S12) is performed after the temperature data and the optical rotating power data are obtained in the temperature changing process.

Specifically, in the data processing step (S12), a regression straight line data between the temperature data and the optical rotating power data obtained by the optical rotating power data acquisition unit 12 is obtained by using the fact that the optical rotating power of the sample is proportional to the measurement temperature.

After the regression straight line data is obtained, the data processing unit 14 uses the obtained regression straight line data to determine the optical rotating power data of the sample at the predetermined temperature.

According to the present embodiment, the optical rotating power data obtained up to the point where the predetermined temperature is reached, which was conventionally discarded, is used to reduce noise, thereby increasing the measurement precision.

In addition, in the present embodiment, since the optical rotating power data of the sample is obtained from the optical rotating power data obtained up to the point where the predetermined temperature is reached, which was conventionally discarded, optical rotating power measurement can be started without waiting for the temperature of the sample to reach the predetermined temperature. Therefore, the measurement can be sped up.

The operation will be described below in more detail.

The sample temperature controller 16 controls the temperature of the sample placed in the sample cell 25 so as to reach the temperature specified in advance. Even if the sample is disposed in the sample cell 25 and the sample temperature controller 16 starts adjusting the temperature, the temperature of the sample generally does not immediately match the specified temperature but differs from the specified temperature for a while, which is called the temperature changing process.

The difference between the specified temperature and the measurement temperature can cause a measurement error. It is, therefore, demanded that measurement be performed, for example, at 20±2° C., and preferably, at 20±0.2° C. Conventionally, measurement was conducted in one of the following ways.

(1) The person in charge of the measurement reads the temperature data of the sample, waits for the temperature data to fall within the requested temperature tolerance, and records the optical rotating power data in an apparatus memory or on a recording sheet.

(2) The measurement apparatus reads the temperature data of the sample, waits for the temperature data to fall within the requested temperature tolerance, and records the optical rotating power data as a valid value.

Figure 2:
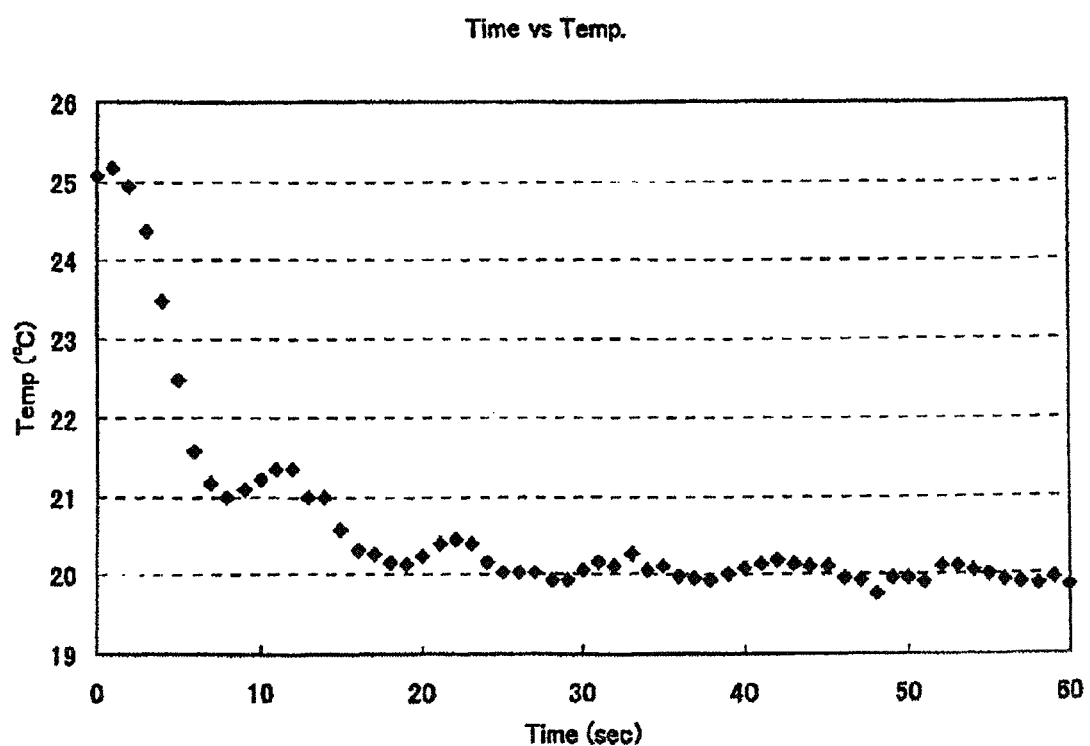
FIG. 2 shows measurement results obtained in 5% saccharose solution by using the sodium D line.
Figure 3:
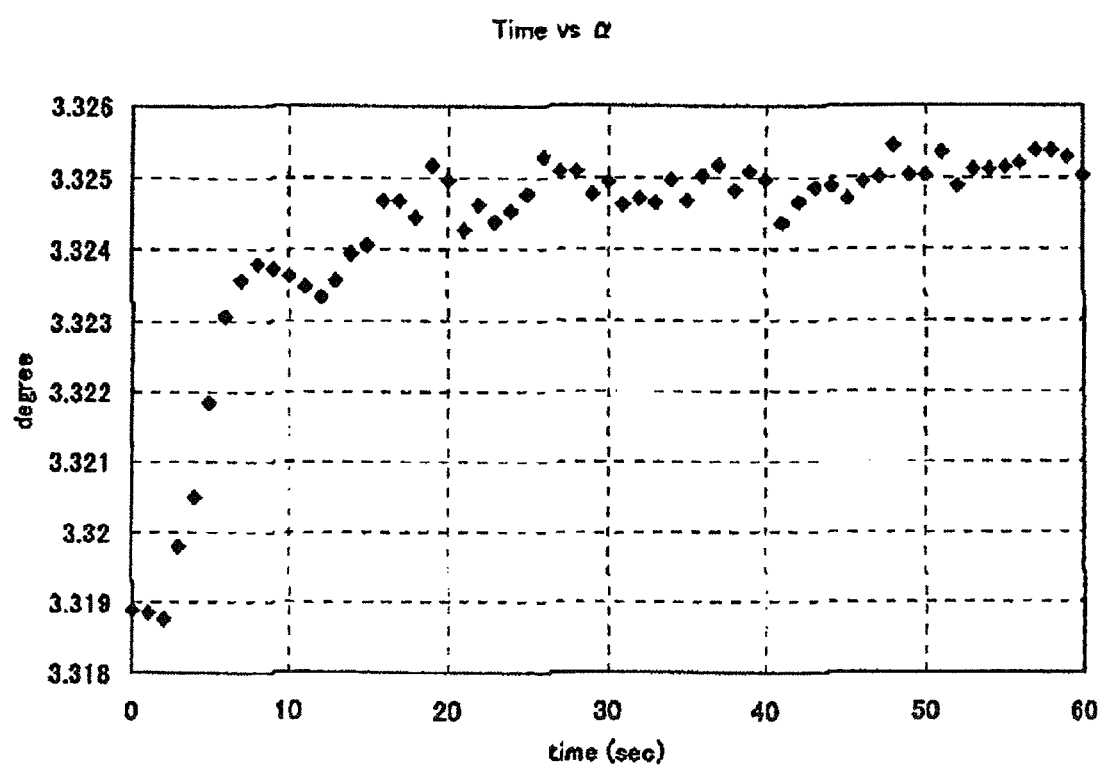
FIG. 3 shows changes of optical rotating power with time after the start of measurement.

FIG. 2 shows measurement results obtained in 5% saccharose solution by using the sodium D line. It is clearly understood from the figure that the temperature data of the sample becomes almost stable about 30 seconds after the sample is introduced (from zero seconds in the figure). FIG. 3 shows time data and optical rotating power data in the measurement shown in FIG. 2.

Conventionally, for example, measurement starts 40 seconds after the sample is introduced, and the average of data measured from 40 seconds to 60 seconds after the sample is introduced is taken.

If the temperature data of the sample is measured and one waits for it to fall within a required temperature tolerance in order to improve the S/N ratio, however, it takes some time until actual measurement starts. The time lag from when the sample is introduced to when measurement starts would be a more serious problem in a sample that experiences a chemical reaction with time and whose optical rotating power changes with time because the correct optical rotating power data cannot be obtained.

Conventionally, since a signal obtained from when the sample is introduced to when the temperature of the sample becomes stable is not used, it does not affect the S/N ratio; however, efficient measurement cannot be performed.

When a quick measurement is attempted conventionally without taking into account S/N ratio improvement, measurement can be started if the temperature data of the sample falls within an allowable range of a few degrees from a predetermined temperature, such as 20±2° C. without waiting for the temperature of the sample to reach a predetermined temperature. However, this attempt may cause a measurement error when the sample has a large temperature coefficient even if the temperature of the sample falls within the allowable range.

In contrast, to ensure both speedup and S/N ratio improvement in measurements, the present embodiment uses the fact that the optical rotating power data of a sample is proportional to the measurement temperature data and uses the optical rotating power data of the sample obtained during the temperature changing process during which the temperature of the sample is changed to a predetermined temperature. Therefore, when measurement is started after the sample is introduced, temperature data and optical rotating power data of the sample are obtained over time during the temperature changing process. As a result, the relationship between the temperature data and the optical rotating power data can be obtained, for example, as shown in FIG. 4.

Figure 4:
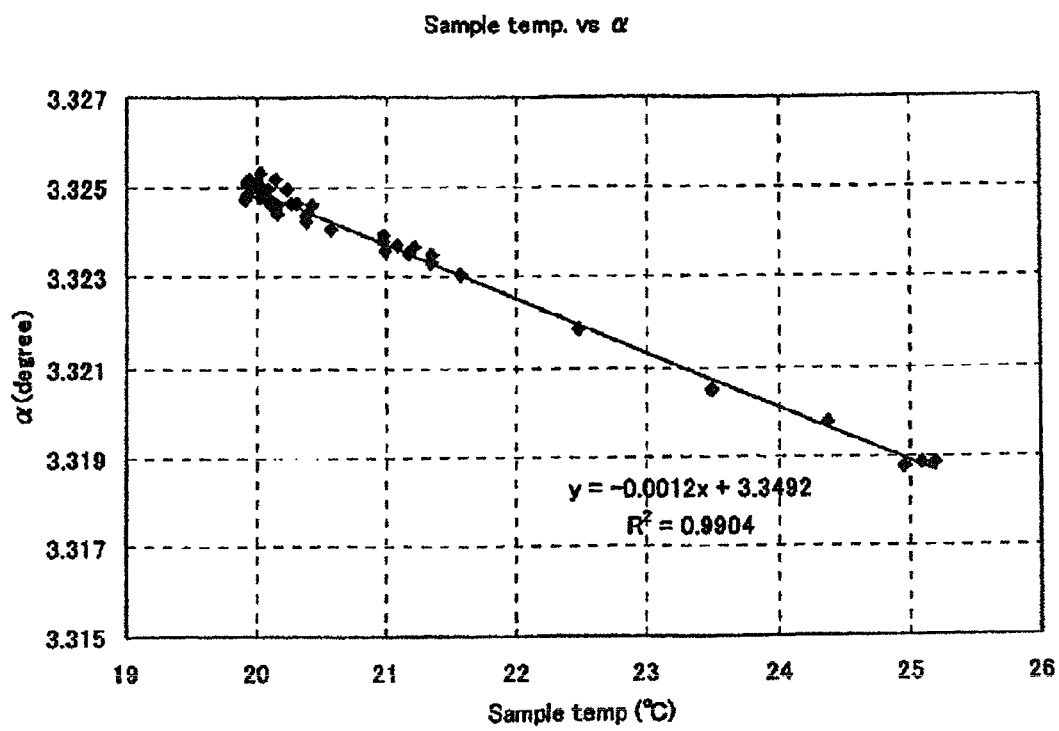
FIG. 4 shows the relationship data between the sample temperature and the optical rotating power from the start of measurement to 40 seconds after the start.

In the present embodiment, by using the fact that the optical rotating power and the temperature of the sample have a linear relationship, the gradient data and intercept data of the linear relationship data between the optical rotating power data and the sample temperature data, with respect to the temperature, are obtained by straight line regression data at 10 seconds, 20 seconds, and 30 seconds after the start of the measurement in the relationship between the temperature data and the optical rotating power data shown in FIG. 4. Then, the optical rotating power data at the predetermined temperature is determined.

The optical rotating power $\alpha$, which is a function of the temperature, can be expressed by Expression 1 below:

$$\alpha = \alpha_0 + kt \quad \text{Expression 1}$$

where $\alpha_0$ indicates the optical rotating power at 0° C., k indicates the change per unit temperature in the optical rotating power, and t indicates the temperature.

From the above data, $\alpha_0$ and k were obtained, and the optical rotating power $\alpha_{20}$ at 20° C. and the specific rotatory power were calculated. The average of measured values obtained from 40 seconds to 60 seconds was calculated with a conventional method. Table 1 shows these results.

Since the present embodiment uses the fact that the optical rotating power is proportional to the specified temperatures in a narrow range of temperatures, if the optical rotating power data obtained at a temperature very far from a predetermined temperature is used, an incorrect optical rotating power data may be obtained at the predetermined temperature. This is a more serious problem if the sample is more highly dependent on the temperature.

Therefore, it is preferred in the present embodiment that a temperature range to be used be specified in the temperature changing process.

Figure 5A:
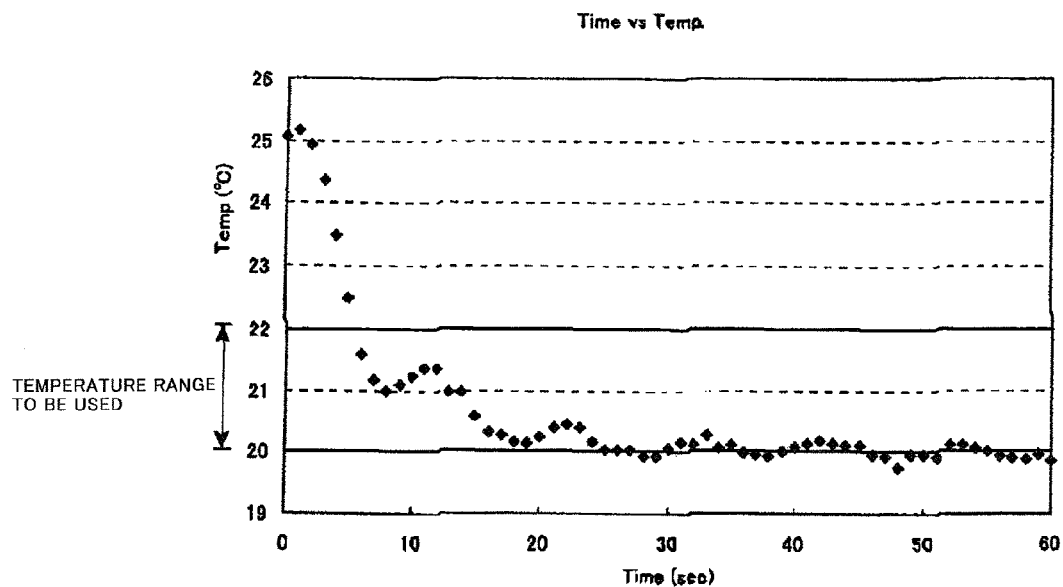
FIGS. 5A and 5B show a preferred temperature range data used in optical rotating power measurement according to the embodiment.

In the present embodiment, for example, an allowable temperature range of +2° C., which is determined according to the temperature dependence data of the sample, is specified for a predetermined temperature of 20° C. to set the temperature range to be used, as shown in FIG. 5A.

Figure 5B:
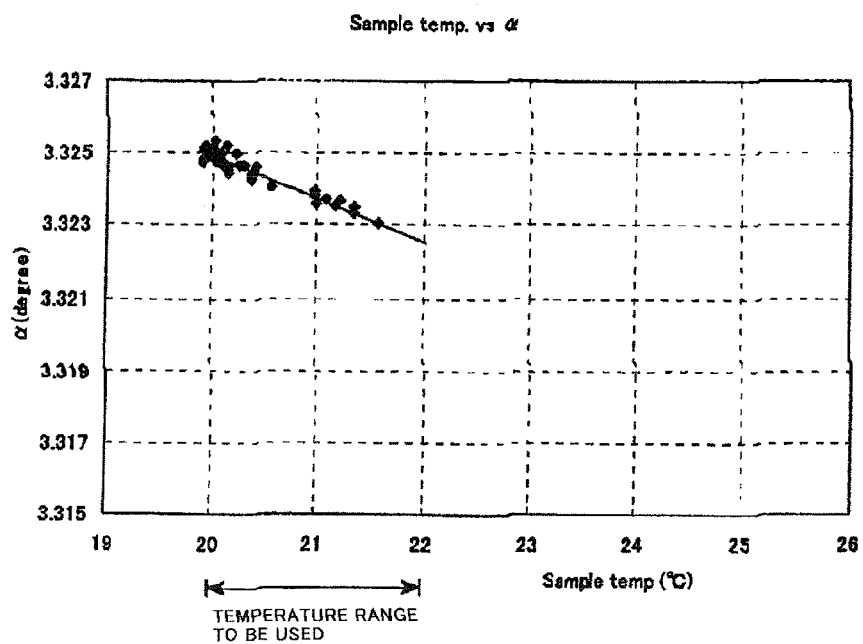

When a regression straight line data is obtained, only optical rotating power data obtained at temperatures that fall within the allowable temperature range is used, as shown in FIG. 5B. In FIG. 5B, optical rotating power data obtained at temperatures that fall within the temperature range from 20° C. to 22° C. is plotted to obtain a regression straight line data.

The regression straight line obtained in this manner is used to determine the optical rotating power at the predetermined temperature, namely in this case, at 20° C.

Since the temperature range of the optical rotating power data used to obtain a regression straight line data is taken into account based on the temperature dependence data of the

TABLE 1

| Measurement method | Measurement period [seconds] | $\alpha_0$ | k | $\alpha_{20}$ | $[\alpha]^{20}_D$ | Temperature coefficient |
|---|---|---|---|---|---|---|
| Conventional | 40-60 | * | * | 3.32504 | 66.50071 | * |
| Present embodiment | 0-10 | 3.349443 | −0.00122 | 3.32501 | 66.50012 | −0.000367 |
| | 0-20 | 3.349523 | −0.00123 | 3.32502 | 66.50037 | −0.000368 |
| | 0-30 | 3.349278 | −0.00121 | 3.32498 | 66.49963 | −0.000365 |

According to JIS K 0063, "Optical-rotating-power measurement method for chemical products", the specific rotatory power of 5 g/100 ml saccharose solution is +66.500 and the temperature coefficient thereof is −0.00037 when the saccharose temperature dependence is expressed by Expression 2 below.

It is clearly understood from Table 1 that the optical rotating power at 20° C. and the temperature coefficient were obtained more precisely in shorter periods in the present embodiment than when the conventional method was used.

$$\alpha^t_D = \alpha^{20}_D[1 - 0.00037(t-20)] \quad \text{Expression 2}$$

As described above, according to the present embodiment, the optical rotating power of a sample at a predetermined temperature is determined according to a regression straight line indicating the relationship between the temperature data and the optical rotating power data of the sample obtained during the temperature changing process during which the temperature of the sample reaches the predetermined temperature. Therefore, both speedup and S/N ratio improvement in measurements are ensured.

Realizing Higher Precision in Measurements
<Temperature Range to be Used>

To further increase measurement precision in the present embodiment, it is preferred that the temperature range of optical rotating power data to be used to obtain a regression straight line be taken into account.

sample, noise data can be reduced and higher measurement precision is provided than when the temperature range is not taken into account.

Realizing More Speedup in Measurements
<Adjustable-temperature Cell Holder>

Conventionally, a water-jacket cell is used and constant-temperature water is supplied from a thermostatic chamber to the water-jacket cell to perform temperature adjustment. In this case, however, the piping and inserting and removing the sample are troublesome.

In order to further speed up the measurements, it is also preferred in the present embodiment to use the following adjustable temperature cell holder, which is compact, easily temperature adjusted, and is capable of being positioned.

Figure 6:
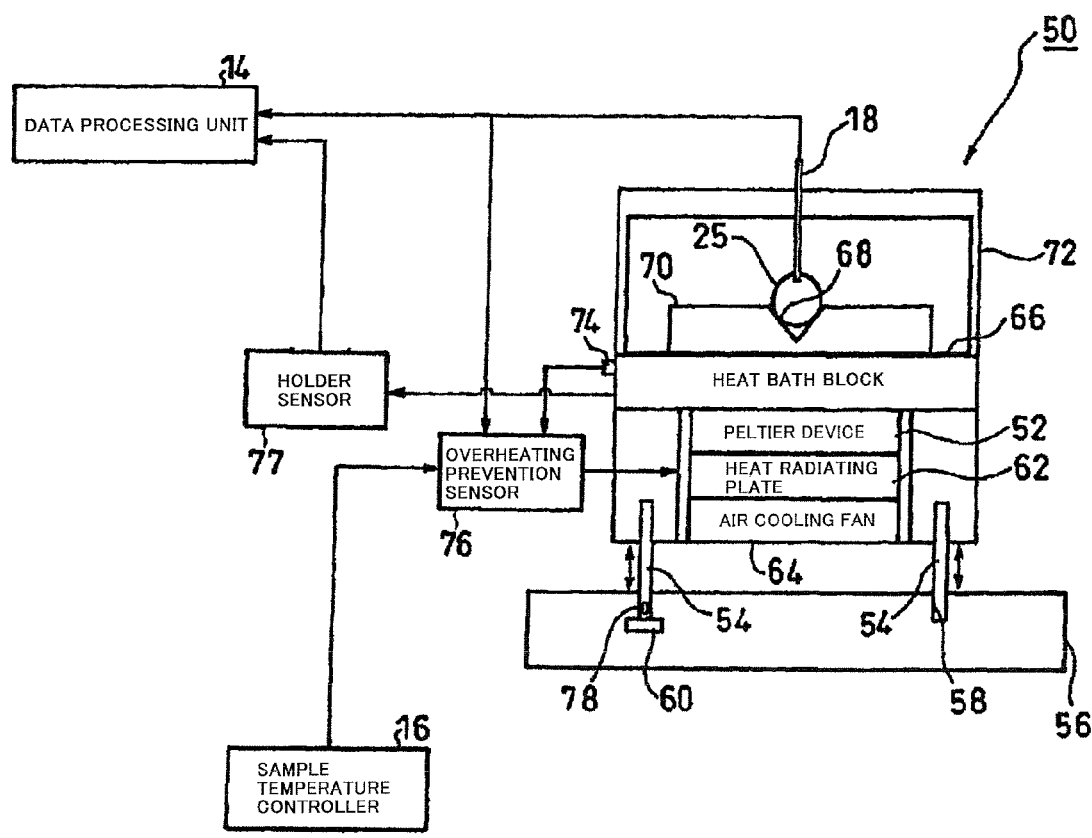
FIG. 6 is a view showing a preferred adjustable temperature cell holder in the optical rotating power measurement according to the embodiment.

FIG. 6 shows, in outline, the structure of the adjustable temperature cell holder 50 for a cylindrical cell.

The adjustable temperature cell holder 50 is cylindrically-shaped and includes a Peltier device 52 and positioning pins 54.

The Peltier device 52 is used to adjust the temperature of the sample placed in the sample cell 25.

The positioning pins (positioning unit) 54 are used to position the center line (measurement axis line) of the sample cell 25 in a predetermined optical path in the optical rotating power measurement apparatus.

The adjustable temperature cell holder 50 is positioned by the positioning pins 54, controls the Peltier device 52, which is forcibly cooled by air, and uses a temperature sensor 18 disposed in a heat-bath block 66 to adjust the temperature of the sample disposed in the sample cell 25.

<Adjustable Temperature Cell Holder>

The adjustable temperature cell holder 50 will be described below in detail.

As shown in FIG. 6, the adjustable temperature cell holder 50 includes a base plate 56, a heat radiating plate 62, an air cooling fan 64, the Peltier device 52, the positioning pins 54, the heat bath block 66, a cell base 70 having a groove 68, a cover 72, a microswitch 74 for monitoring sensor installation, an overheating prevention sensor 76, a holder sensor 77, and an attachment recognition IC 78.

The base plate 56 is used to place the adjustable temperature cell holder 50 on a base of the optical rotating power measurement apparatus 10. The base plate 56 includes positioning holes 58 and an attachment recognition connector 60. The positioning holes 58 are used to position the positioning pins 54. When the positioning pins 54 are positioned at the positioning holes 58, the adjustable temperature cell holder 50 is placed at a predetermined position in the optical rotating power measurement apparatus 10. The attachment recognition connector 60 is used to detect attachment recognition information stored in the attachment recognition IC 78.

The heat radiating plate 62 radiates the heat of the Peltier device 52.

The air cooling fan 64 is provided for the heat radiating plate 62 and forcibly air-cools the Peltier device 52 through the heat radiation plate 62.

The Peltier device 52 controls the temperature of the sample depending on the direction and magnitude of DC current supplied to the Peltier device 52.

The heat bath block 66 is placed between the sample cell 25 and the Peltier device 52. Temperature adjustment is applied to the sample cell 25 from the Peltier device 52 through the heat bath block 66. The heat bath block 66 is connected to the holder sensor 77, and the holder sensor 77 is connected to the data processing unit 14.

The cell base 70 holds the sample cell 25 at the groove 68.

The cover 72 is placed on the heat bath block 66 from above. With this cover 72, the temperature of the sample is easier to adjust.

The microswitch 74 monitors the installation of the temperature sensor 18. Whether the temperature sensor 18 has been installed, whether the temperature sensor 18 has been installed properly, and other conditions can be checked with the microswitch 74. Therefore, correct temperature data can be obtained.

The overheating prevention sensor 76 prevents the adjustable temperature cell holder 50 from being overheated.

The attachment recognition IC 78 stores the attachment recognition information. In combination with the attachment recognition connector 60, information about attachment can be easily obtained.

As described above, in the present embodiment, the temperature of the sample can be easily made to reach a predetermined temperature with the temperature control performed by the Peltier device 52. Therefore, the change in temperature with time until required thermal equilibrium is reached can be obtained easily. Consequently, the present embodiment further speeds up the measurements compared with a standard water-jacket cell.

In addition, the sample cell 25 can be easily positioned by using the positioning pins 54 such that the center of the sample cell 25 is aligned with the optical path in the measurement. Therefore, a plurality of cylindrical cells having different diameters can be easily positioned. Consequently, the present embodiment further speeds up the measurements compared with a standard water-jacket cell.

The sample cell 25 just needs to be placed on the groove 68 of the cell base 70. Therefore, the present embodiment further speeds up the measurements compared with the conventional method, where the water jacket needs to be mounted and removed every time the sample cell 25 is inserted and removed, because the piping is simpler and insertion and removal of the sample are facilitated.

In the present embodiment, in cases where optical rotating power data obtained during the temperature changing process is used, the optical rotating power data can be estimated after the actual measurement period by using a regression straight line data, and further, optical rotating power data at the predetermined temperature under thermal equilibrium can be used.

By using the regression straight line data, not only can the optical rotating power data at the predetermined temperature be obtained but it is also possible to determine the temperature dependence data of the optical rotating power of the sample.

What is claimed is:

1. An optical rotating power measurement method for obtaining optical rotating power data of a sample at a predetermined temperature by using an optical rotating power measurement apparatus provided with a sample temperature controller for controlling the temperature of the sample such that the temperature reaches the predetermined temperature, comprising:

an optical rotating power data acquisition step of obtaining two or more temperature data and optical rotating power data of the sample at each of the temperature data during a temperature changing process where the sample temperature controller controls the temperature of the sample such that the temperature reaches the predetermined temperature; and a data processing step of setting a temperature range of the optical rotating power data used to obtain a regression straight line data based on temperature dependence data of the sample, and obtaining the regression straight line from the temperature data and the corresponding optical rotating power data within the temperature range;

wherein the optical rotating power data of the sample at the predetermined temperature is determined based on the regression straight line.

2. An optical rotating power measurement apparatus for obtaining optical rotating power data of a sample at a predetermined temperature, comprising:

a sample temperature controller for controlling the temperature of the sample such that the temperature reaches the predetermined temperature, the sample temperature controller comprising an adjustable temperature cell holder for holding a sample cell while controlling the temperature of the sample such that the temperature reaches the predetermined temperature;

an optical rotating power data acquisition unit for obtaining two or more temperature data and optical rotating power data of the sample at each of the temperature data during a temperature changing process where the sample temperature controller controls the temperature of the sample such that the temperature reaches the predetermined temperature; and a data processing unit for setting a temperature range of the optical rotating power data used to obtain a regression straight line data based on temperature dependence data of the sample, and obtaining the regression straight line from the temperature data and the corresponding optical rotating power data within the temperature range;

wherein the optical rotating power data of the sample at the predetermined temperature is determined based on the regression straight line.

3. An optical rotating power measurement apparatus according to claim 2, wherein the adjustable temperature cell holder comprises a Peltier device for adjusting the temperature of the sample disposed in the sample cell.

4. An optical rotating power measurement apparatus according to claim 2, wherein the adjustable temperature cell holder comprises a positioning unit for positioning the adjustable temperature cell holder such that a measurement axis located at the center of the sample cell is positioned on a predetermined optical path of the optical rotating power measurement apparatus.

5. An optical rotating power measurement apparatus according to claim 3, wherein the adjustable temperature cell holder comprises a positioning unit for positioning the adjustable temperature cell holder such that a measurement axis located at the center of the sample cell is positioned on a predetermined optical path of the optical rotating power measurement apparatus.

* * * * *